United States Patent
Ashmore et al.

(10) Patent No.: US 10,398,309 B2
(45) Date of Patent: *Sep. 3, 2019

(54) NONINVASIVE RAPID SCREENING OF MILD TRAUMATIC BRAIN INJURY USING COMBINATION OF SUBJECT'S OBJECTIVE OCULOMOTOR, VESTIBULAR AND REACTION TIME ANALYTIC VARIABLES

(71) Applicant: Neuro Kinetics, Inc., Pittsburgh, PA (US)

(72) Inventors: Robin C. Ashmore, Pittsburgh, PA (US); Howison Schroeder, Pittsburgh, PA (US); Daniel Sweeney, Pittsburgh, PA (US); Alexander D Kiderman, Pittsburgh, PA (US); Robert Sclabassi, Pittsburgh, PA (US); Thomas Joos, Pittsburgh, PA (US); Greg Frank, Pittsburgh, PA (US); Thomas Vernon Baker, Wayzata, MN (US)

(73) Assignee: NEURO KINETICS, INC., Pittsburgh, PA (US)

( * ) Notice: Subject to any disclaimer, the term of this patent is extended or adjusted under 35 U.S.C. 154(b) by 1108 days.

This patent is subject to a terminal disclaimer.

(21) Appl. No.: 14/687,871

(22) Filed: Apr. 15, 2015

(65) Prior Publication Data
US 2015/0335278 A1 Nov. 26, 2015

Related U.S. Application Data

(63) Continuation-in-part of application No. 14/336,254, filed on Jul. 21, 2014, now Pat. No. 9,039,632, which
(Continued)

(51) Int. Cl.
*A61B 5/00* (2006.01)
*A61B 3/113* (2006.01)
(Continued)

(52) U.S. Cl.
CPC ............ *A61B 3/113* (2013.01); *A61B 3/0041* (2013.01); *A61B 3/14* (2013.01); *A61B 5/16* (2013.01);
(Continued)

(58) Field of Classification Search
CPC ........... A61B 3/02; A61B 3/032; A61B 3/113; A61B 3/4064
See application file for complete search history.

(56) References Cited

U.S. PATENT DOCUMENTS 3,612,642 A 10/1971 Dostal
4,006,974 A 2/1977 Resnick
(Continued)

FOREIGN PATENT DOCUMENTS

JP 11/184621 7/1999

OTHER PUBLICATIONS

Jason S. Babcock, Jeff B. Pelz, Building a lightweight eyetracker, http://www.cis.rit.edu/people/faculty/pelz/publications/ETRA04_babcock_pelz.pdf, 2004.
(Continued)

*Primary Examiner* — Max F Hindenburg
(74) *Attorney, Agent, or Firm* — Blynn L. Shideler; Krisanne Shideler; BLK Law Group

(57) ABSTRACT

A portable VOG device is disclosed that will facilitate the effective and efficient screening for TBI in military personnel in forward deployed military settings or remote locations using minimally trained staff. This includes the establishment of a protocol that will provide cost effective pre-screening of military personnel prior to deployment to establish a baseline of brain function prior to possible future injury. The efficiency of the device will promote subsequent follow-up screening to assess the effectiveness of prescribed TBI treatment. Further protocols for diagnosis and rehabili-
(Continued)

tation applications using the same virtual reality portable device will allow more advanced usage for clinicians providing ongoing evaluation and treatment.

20 Claims, 1 Drawing Sheet

Related U.S. Application Data is a continuation of application No. 14/083,145, filed on Nov. 18, 2013, now Pat. No. 9,039,631, which is a continuation-in-part of application No. 12/577,143, filed on Oct. 9, 2009, now Pat. No. 8,585,609.

(60) Provisional application No. 61/979,765, filed on Apr. 15, 2014, provisional application No. 61/104,133, filed on Oct. 9, 2008.

(51) Int. Cl.
*A61B 3/14* (2006.01)
*A61B 3/00* (2006.01)
*A61B 5/16* (2006.01)
*G02B 27/01* (2006.01)
*G02B 27/00* (2006.01)

(52) U.S. Cl.
CPC .......... *A61B 5/4064* (2013.01); *A61B 5/6803* (2013.01); *G02B 27/017* (2013.01); *A61B 5/4863* (2013.01); *G02B 27/0093* (2013.01); *G02B 2027/014* (2013.01); *G02B 2027/0138* (2013.01); *G02B 2027/0187* (2013.01)

(56) References Cited

U.S. PATENT DOCUMENTS

| | | |
|---|---|---|
| 4,084,182 A | 4/1978 | Maiman |
| 4,309,608 A | 1/1982 | Adamson |
| 4,320,768 A | 3/1982 | Ledley et al. |
| 4,474,186 A | 10/1984 | Ledley et al. |
| 4,572,199 A | 2/1986 | LaCourse |
| 4,836,219 A | 6/1989 | Hobson et al. |
| 4,852,988 A | 8/1989 | Velez et al. |
| 4,863,259 A | 9/1989 | Schneider et al. |
| 5,070,883 A | 12/1991 | Kasahara |
| 5,098,426 A | 3/1992 | Sklar et al. |
| 5,130,838 A | 7/1992 | Tanaka et al. |
| 5,252,999 A | 10/1993 | Sukigara et al. |
| 5,304,112 A | 4/1994 | Mrklas et al. |
| 5,305,746 A | 4/1994 | Fendrock |
| 5,320,109 A | 6/1994 | Chamoun et al. |
| 5,345,281 A | 9/1994 | Taboada et al. |
| 5,365,941 A | 11/1994 | Yoshimatsu |
| 5,368,041 A | 11/1994 | Shambroom |
| 5,381,804 A | 1/1995 | Shambroom |
| 5,410,376 A | 4/1995 | Cornsweet et al. |
| 5,458,117 A | 10/1995 | Chamoun et al. |
| 5,481,622 A | 1/1996 | Gerhardt |
| 5,491,492 A | 2/1996 | Knapp |
| 5,652,756 A | 7/1997 | Stultz et al. |
| 5,687,020 A | 11/1997 | Park et al. |
| 5,704,369 A | 1/1998 | Scinto |
| 5,714,967 A | 2/1998 | Okamura et al. |
| 5,792,069 A | 8/1998 | Greenwald et al. |
| 5,813,404 A | 9/1998 | Devlin et al. |
| 5,821,521 A | 10/1998 | Bridgelall et al. |
| 5,838,420 A | 11/1998 | MacGregor Donaldson |
| 5,877,732 A | 3/1999 | Ziarati |
| 5,892,566 A | 4/1999 | Bullwinkel |
| 5,942,954 A | 8/1999 | Galiana |
| 5,943,116 A | 8/1999 | Zeimer |
| 5,963,300 A | 10/1999 | Horwitz |
| 5,980,513 A | 11/1999 | Frey et al. |
| 5,983,128 A | 11/1999 | Baudonniere |
| 6,003,991 A | 12/1999 | Virre |
| 6,024,707 A | 2/2000 | Scinto |
| 6,032,064 A | 2/2000 | Devlin et al. |
| 6,032,072 A | 2/2000 | Greenwald et al. |
| 6,033,073 A | 3/2000 | Potapova |
| 6,077,237 A | 6/2000 | Campbell |
| 6,089,716 A | 7/2000 | Lashkari et al. |
| 6,090,051 A | 7/2000 | Marshall |
| 6,099,124 A | 8/2000 | Hadaji |
| 6,113,237 A | 9/2000 | Ober |
| 6,120,461 A | 9/2000 | Smyth |
| 6,162,186 A | 12/2000 | Scinto |
| 6,213,943 B1 | 4/2001 | Abreu |
| 6,231,187 B1 | 5/2001 | Munoz |
| 6,247,813 B1 | 6/2001 | Kim et al. |
| 6,271,915 B1 | 8/2001 | Frey et al. |
| 6,275,718 B1 | 8/2001 | Lempert |
| 6,299,308 B1 | 10/2001 | Veronka et al. |
| 6,367,932 B1 | 4/2002 | Donaldson |
| 6,402,320 B1 | 6/2002 | Borchert |
| 6,456,261 B1 | 9/2002 | Zhang |
| 6,459,446 B1 | 10/2002 | Harman |
| 6,467,905 B1 | 10/2002 | Stahl |
| 6,637,883 B1 | 1/2003 | Tengshe |
| 6,524,581 B1 | 2/2003 | Adamis |
| 6,542,081 B2 | 4/2003 | Torch |
| 6,551,575 B1 | 4/2003 | Greenspan |
| 6,568,808 B2 | 5/2003 | Campin |
| 6,574,352 B1 | 6/2003 | Skolmoski |
| 6,609,523 B1 | 8/2003 | Anthony |
| 6,629,935 B1 | 10/2003 | Miller |
| 6,631,989 B2 | 10/2003 | Odom et al. |
| 6,634,749 B1 | 10/2003 | Morrison et al. |
| 6,652,458 B2 | 11/2003 | Blazey |
| 6,659,611 B2 | 12/2003 | Amir et al. |
| 6,669,341 B2 | 12/2003 | Wirth |
| 6,697,894 B1 | 2/2004 | Mitchell et al. |
| 6,748,275 B2 | 6/2004 | Lattner |
| 6,796,947 B2 | 9/2004 | Watt |
| 6,800,062 B2 | 10/2004 | Epley |
| RE38,668 E | 12/2004 | Edwards |
| 6,943,754 B2 | 9/2005 | Aughey et al. |
| 7,115,099 B2 | 10/2006 | Miller et al. |
| 7,398,119 B2 | 7/2008 | Lambert et al. |
| 7,448,751 B2 | 11/2008 | Kiderman et al. |
| 7,520,614 B2 | 4/2009 | Joos et al. |
| 7,651,224 B2 | 1/2010 | Wood et al. |
| 7,665,845 B2 | 2/2010 | Kiderman et al. |
| 7,819,818 B2 | 10/2010 | Ghajar |
| 7,988,287 B1 | 8/2011 | Butler et al. |
| 8,065,240 B2 | 11/2011 | Jung et al. |
| 8,333,472 B2 | 12/2012 | Kiderman |
| 8,406,859 B2 | 3/2013 | Zuzak et al. |
| 8,568,311 B2 | 10/2013 | LaPlaca et al. |
| 8,585,609 B2 | 11/2013 | Kidderman et al. |
| 9,039,631 B2 | 5/2015 | Kiderman |
| 9,039,632 B2 | 5/2015 | Kiderman |
| 2002/0027779 A1 | 3/2002 | Cassarly |
| 2002/0085174 A1 | 7/2002 | Bolger |
| 2002/0171805 A1 | 11/2002 | Odom et al. |
| 2002/0175880 A1 | 11/2002 | Melville |
| 2003/0028081 A1 | 2/2003 | Blazey |
| 2004/0181168 A1 | 3/2004 | Plant |
| 2005/0004489 A1 | 1/2005 | Sarkela et al. |
| 2005/0024586 A1 | 2/2005 | Teiwes |
| 2005/0216243 A1 | 3/2005 | Graham |
| 2005/0079636 A1 | 4/2005 | White |
| 2005/0099601 A1 | 5/2005 | MacDougall et al. |
| 2005/0101877 A1 | 5/2005 | Miller |
| 2005/0110950 A1 | 5/2005 | Thorpe |
| 2006/0098087 A1 | 5/2006 | Brandt et al. |
| 2006/0235331 A1 | 10/2006 | Kiderman |
| 2007/0132841 A1 | 6/2007 | MacDougall et al. |
| 2008/0273084 A1 | 11/2008 | MacDougall et al. |
| 2008/0278685 A1 | 11/2008 | MacDougall et al. |
| 2009/0118593 A1 | 5/2009 | Jung et al. |
| 2009/0119154 A1 | 5/2009 | Jung et al. |
| 2009/0132275 A1 | 5/2009 | Jung et al. |

(56) References Cited

U.S. PATENT DOCUMENTS

| | | |
|---|---|---|
| 2009/0307179 A1 | 10/2009 | Colby et al. |
| 2009/0307180 A1 | 10/2009 | Colby et al. |
| 2009/0307181 A1 | 10/2009 | Colby et al. |
| 2009/0299645 A1 | 12/2009 | Colby et al. |
| 2010/0280372 A1 | 11/2010 | Poolman et al. |
| 2011/0086914 A1 | 4/2011 | Bailes |
| 2011/0208060 A1 | 8/2011 | Haase et al. |
| 2011/0229862 A1 | 8/2011 | Parikh |
| 2012/0330178 A1 | 10/2012 | Kraft et al. |
| 2014/0192326 A1 | 7/2014 | Kiderman |

OTHER PUBLICATIONS

D. Zhu et al., Computer Methods and Programs in Biomedicine 59 (1999), pp. 146-157.

Abstract of Y Chiba, M.D. and N. Furuya. M.D.; Aging and Reference Values of the Parameters in Optokinetic Nystagmus; 1989; Oto-Rhino-Laryngological Society of Japan; p. 1416-1423.

Abstract of K. Yamada, K. Kaga, N. Furuya;Computer Analysis of the Optokinetic Pattern Test in Acoustic Tumors, Brain Stem and Cerebellar Lesions;Acta Otolaryngol (Stockh) 1991; Suppl. 48.

Cohen B, Matsuo V, Raphan T.; Quantitative analysis of the velocity characteristics of optokinetic nystagmus and optokinetic after-nystagmus.;J. Physiol. (1977), 270, p. 321-324.

Abstract of Kanayama R;Kato I;Nakamura T;Koike Y;The Fast-phase Velocity of Optokinetic Nystagmus in Central Nervous System Disorders;Nov.-Dec. 1987; 104(5-6):39Informa Healthcare, London.

NONINVASIVE RAPID SCREENING OF MILD TRAUMATIC BRAIN INJURY USING COMBINATION OF SUBJECT'S OBJECTIVE OCULOMOTOR, VESTIBULAR AND REACTION TIME ANALYTIC VARIABLES

RELATED APPLICATIONS

This application claims the benefit of U.S. Patent Application 61/979,765 filed Apr. 15, 2014 entitled "Noninvasive Rapid Screening of Mild Traumatic Brain Injury Using Combination of Subject's Objective Oculomotor, Vestibular and Reaction Time Analytic Variables."

This application is a Continuation in Part of U.S. patent application Ser. No. 14/336,254 filed Jul. 21, 2014 and entitled "Quantitative, Non-Invasive, Clinical Diagnosis of Traumatic Brain Injury Using VOG Device for Neurologic Testing" which published Nov. 6, 2014 as U.S. Patent Publication 2014-0327880 which is incorporated herein by reference. U.S. patent application Ser. No. 14/336,254 has now issued U.S. Pat. No. 9,039,632.

U.S. patent application Ser. No. 14/336,254 is a Continuation of U.S. patent application Ser. No. 14/083,145 filed Nov. 18, 2013 and entitled "Quantitative, Non-Invasive, Clinical Diagnosis of Traumatic Brain Injury Using VOG Device for Neurologic Testing" which published Jul. 10, 2010 as U.S. Patent Publication 2014-0192326 which is incorporated herein by reference. U.S. patent application 14/083,145 has now issued as U.S. Pat. No. 9,039,631

U.S. patent application Ser. No. 14/083,145 is a Continuation in Part of U.S. patent application Ser. No. 12/577,143 filed Oct. 9, 2009 and entitled "Quantitative, Non-Invasive, Clinical Diagnosis of Traumatic Brain Injury Using Simulated Distance Visual Stimulus Device for Neurologic Testing". U.S. patent application Ser. No. 12/577,143 published as U.S. Publication Number 2010-0094161 on Apr. 15, 2010, and issued as U.S. Pat. No. 8,585,609 on Nov. 19, 2013, which publication and patent are incorporated herein by reference.

U.S. patent application Ser. No. 12/577,143 claims the benefit of U.S. Provisional patent application Ser. No. 61/104,133 filed Oct. 9. 2008 entitled "Quantitative, Non-Invasive, Clinical Diagnosis of Traumatic Brain Injury."

BACKGROUND OF THE INVENTION

1. Field of the Invention

The present invention relates to Traumatic Brain Injury (TBI including mild Traumatic Brain Injury or mTBI) and psychological health, and more specifically to quantitative, noninvasive, clinical diagnosis of traumatic brain injury, particularly for military applications. The present invention is directed to noninvasive rapid screening of mild traumatic brain injury using combination of subject's objective oculomotor, vestibular and reaction time analytic variables.

2. Background Information

Traumatic Brain Injury (TBI) is the result of a blunt blow, jolt or blast overpressure to the head that disrupts brain function. The subset of mild TBI, or mTBI, has represented a harder segment of TBI to diagnose. Within this application mTBI is a subset of TBI. The terms mild TBI (mTBI) and concussion are commonly used interchangeably in the art, and have been linked with Post Traumatic Stress Disorder. The severity of head injuries range from a brief change in mental status or consciousness to extended unconsciousness and amnesia. In severe or multiple concussion cases, personality changes can occur with devastating results.

Military personnel, despite using strong protective devices, frequently suffer blast injuries to the head. In a study conducted at the Walter Reed Army Medical Center, 62% of Operation Iraqi Freedom combat wounded troops showed symptoms of mild to severe brain injuries and of these, 91.6% had possibly sustained a TBI injury as a result of a blast. A number of recent studies have substantiated the presence of vestibular deficits in the acute period following TBI. The Defense and Veterans Brain Injury Center (www.dvbic.org) is a part of the U.S. Military Health System, specifically, it is the traumatic brain injury (TBI) operational component of the Defense Centers of Excellence for Psychological Health and Traumatic Brain Injury (DCoE) founded in 1992 by Congress, and represent a source for further detailed background and state of the art for TBI and the effect on the military.

Proper treatment of TBI injury requires an accurate diagnosis of the structures affected. Proper treatment of TBI injury requires an accurate diagnosis of the structures affected. The mechanisms of injury in TBI cause a variety of abnormalities in the peripheral vestibular mechanisms, central vestibular structures, ocular-motor tracts, cerebellum, as well as all portions of the brain communicating with these structures. The onset of vestibular deficits generally occurs within seven to ten days post injury. While reported symptoms of dizziness resolve after three months, 15% have persistent symptoms one year later.

Existing screening and diagnostic tools employed on patients with balance and neurological disorders associated with TBI based on the traditional battery of vestibular, balance and neurological tests requires the use of large stationary systems (neuro-otologic test center, Barany/rotary chair, ENG/VNG, computerized posturography/balance platforms, etc.). These large systems deploy a full battery of ocular motor, motion, artificial motion, balance and combined tests. Utilizing such devices may be practical in hospital settings, but are not useful in forward deployed military settings, or remote locations, such as first responder emergency medical technicians (EMTs).

The Centers for Disease Control and Prevention estimates that at least 3.17 million Americans currently have a long-term or lifelong need for help to perform activities of daily living as a result of a TBI. Currently there is no accepted clinical method to objectively detect mTBI. The Center for Disease Control (at http://www.cdc.gov/TraumaticBrainInjury/statistics.html) estimates that "About 75% of TBIs that occur each year are concussions or other forms of mild TBI." For further background please see Brain Injury Association of America at www.BIAUSA.org as The Brain injury Association of America (BAN) is the country's oldest and largest nationwide, brain injury advocacy organization.

For background on TBI assessment systems see U.S. Pat. No. 8,568,311 developed by Emory University which discloses an immersive cognitive assessment system which suppresses outside video and audio inputs. The '311 patent, which is incorporated herein by reference, discloses a distinct approach to the TBI assessment and is helpful to further establish the state of the art, including a relatively comprehensive listing of publications in the field.

It is the object of the present invention to address the deficiencies of the prior art.

SUMMARY OF THE INVENTION

The present invention is drawn to the development of a portable VOG device that will facilitate the effective and efficient screening for TBI in subjects such as military personnel in forward deployed military settings or remote locations using minimally trained staff.

One aspect of the invention provides a method of diagnosis of traumatic brain injury comprising the steps of: providing a stimulus generating eye tracking unit, such as a head mounted goggle based eye tracking unit coupled to the subject; presenting a plurality of virtual reality based visual stimulus to the subject, wherein at least one visual stimulus is at a simulated distance in the eye tracking unit, wherein each visual stimulus provides a target stimulus for a visual based neurologic test; obtaining objective physiologic response of the subject from the eye tracking unit based upon each of neurologic test associated with each visual stimulus presented to the subject; and using the objective physiologic responses to the neurologic tests to diagnose the presence of traumatic brain injury.

The method of diagnosis of traumatic brain injury according to the invention may provide that the visual stimulus presented to the subject includes nystagmus tests, such as at least one horizontal nystagmus test, one vertical and one spontaneous nystagmus test. The visual stimulus presented to the subject may include at least one horizontal smooth pursuit test and at least one vertical smooth pursuit test. The visual stimulus presented to the subject may include at least one horizontal saccades test and at least one vertical saccades test.

The step of using the objective physiologic responses to diagnose the presence of traumatic brain injury may include determining whether at least one post-trauma objective physiologic responses of the subject differs from an associated objective physiologic response of a normative database of similar subjects by greater than a preset threshold for that response. The method of diagnosis of traumatic brain injury according to invention may further include the step of obtaining pre-trauma objective physiologic responses of the subject from the head mounted goggle unit based upon each of the visual stimulus presented to the subject, wherein the pre-trauma objective physiologic responses form a baseline for the subject.

One implementation of the present invention includes the establishment of a protocol that will provide cost effective pre-screening of military personnel prior to deployment to establish a baseline of brain function prior to possible future injury. The efficiency of the device will promote subsequent follow-up screening to assess the effectiveness of prescribed TBI treatment. Further protocols for diagnosis and rehabilitation applications using the same virtual reality portable device will allow more advanced usage for clinicians providing ongoing evaluation and treatment.

The present invention provides a simple, quantitative, noninvasive method to diagnose TBI including mTBI that can be used for deployed troops; efficient clinical diagnostic criteria methodologies for detecting TBI, while distinguishing it from psychological co-morbidities; Innovative therapies for TBI; and an impact on rehabilitation strategies on neural plasticity and neurogenesis following TBI.

These and other advantages are described in the brief description of the preferred embodiments in which like reference numeral represent like elements throughout.

DESCRIPTION OF THE PREFERRED EMBODIMENTS

It is noted that, as used in this specification and the appended claims, the singular forms "a," "an," and "the" include plural referents unless expressly and unequivocally limited to one referent.

Figure 1:
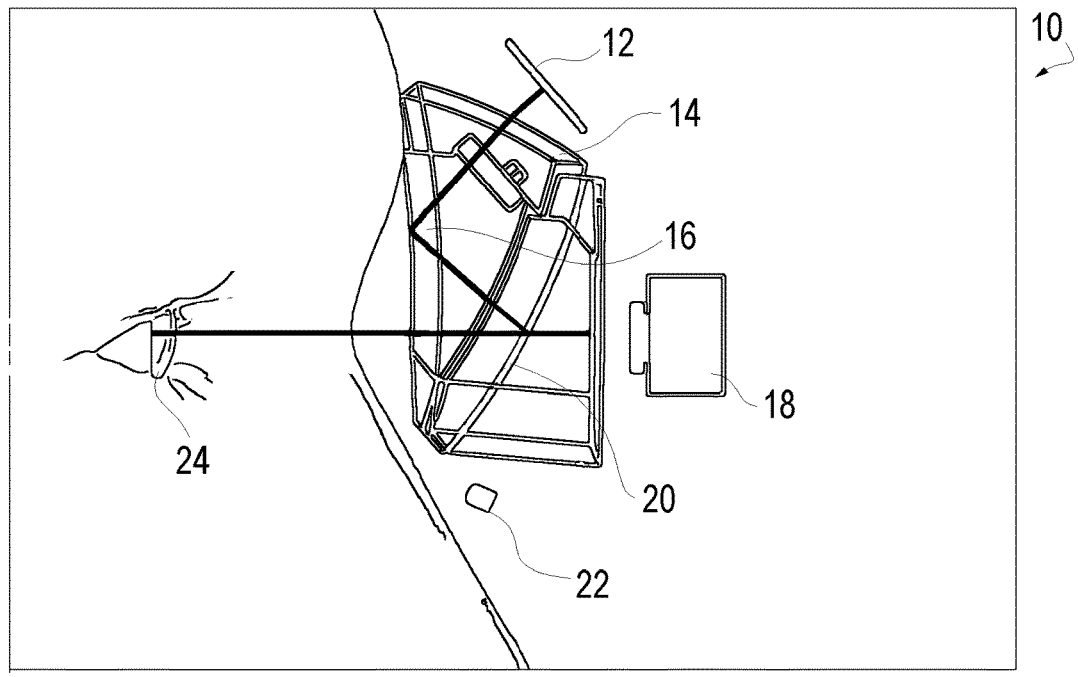
FIG. 1 is schematic representation of a portable virtual reality device that will facilitate the effective and efficient screening for TBI in accordance with the present invention.
Figure 2:
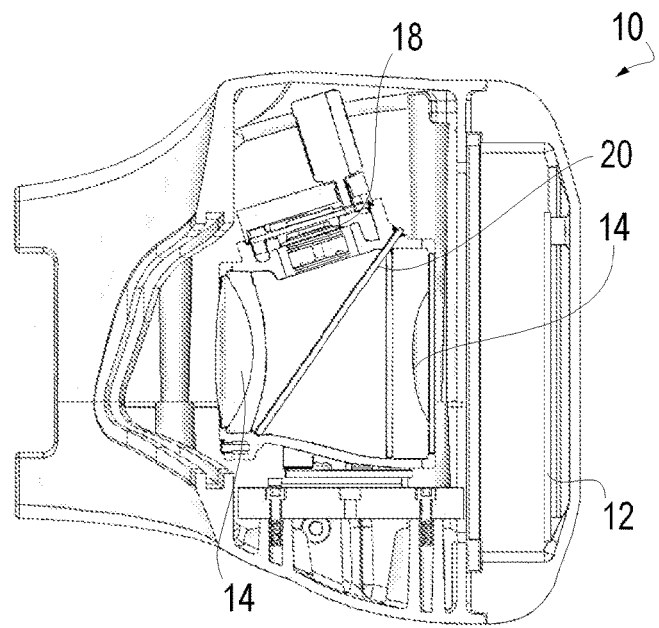
FIG. 2 is schematic representation of an alternative portable virtual reality device that will facilitate the effective and efficient screening for TBI in accordance with the present invention.

The method of diagnosis of traumatic brain injury according to one aspect of the invention comprising the steps of: providing a stimulus generating eye tracking unit 10 (examples of which are shown in FIGS. 1 and 2), such as a head mounted goggle based eye tracking unit that can present virtual reality based visual targets to the subject. The unit 10 as shown may be categorized as a type of Video-oculography (VOG) system, which as accurately defined by Richard E. Gans, PhD, who is the Founder and Executive Director of the American Institute of Balance and he served on the board of the American Academy of Audiology, in the Hearing Journal: May 2001—Volume 54—Issue 5—pp 40, 42 "Video-oculography is a method of recording eye movement through the use of digital video cameras. This is a significant change from electronystagmography, which uses the corneal retinal potential, which is the eye's battery-like effect. As the eyes move side to side and up and down, the corneo-retinal potential's positive and negative discharge is recorded. VOG technology, however, uses infrared cameras to measure the eye's position. Small cameras, mounted in goggles, track the center of the pupil to provide the location of the eye."

Videonystagmograpy (VNG) is often defined as a technology for testing inner ear and central motor functions, a process known as vestibular assessment and is defines as involving the use of infrared goggles to trace eye movements during visual stimulation and positional changes. A VNG unit is typically a diagnostic system for recording, analyzing and reporting (generally) involuntary eye movements, called nystagmus for involuntary movements, using video imaging technology. The eye tracking unit 10, as described in greater detail below, may also be defined as a VNG system. VNG systems are considered, for the purpose of this application, to be a subset of the broader VOG terminology The VOG/VNG unit 10 coupled to the subject; presenting a plurality of visual stimulus to the subject, wherein the visual stimulus may be at a simulated distance in the eye tracking unit, wherein substantially each visual stimulus provides a target stimulus for a visual based neurologic test; obtaining objective physiologic response of the subject from the eye tracking unit based upon each of neurologic test associated with each visual stimulus presented to the subject; and using the objective physiologic responses to the neurologic tests to diagnose the presence of traumatic brain injury.

Virtual environment exposure, also called virtual reality or VR, has proven highly efficient and effective in vestibular rehabilitation since the experience gained during VR exposure is transferable to the real world. The VR technology in the present invention is used to accurately provide a simulated distance to a visual target, if needed, for performing a variety of standard neurologic tests on the subject.

Additionally, the VR use in the rehabilitation of TBI accelerates the compensation of an acute loss of peripheral or central vestibular function by improving adaptive modifications of the vestibulo-ocular reflex. This device has the substantial and tremendous potential of being used bedside and in the home to increase rehabilitation compensation speed and degree.

Innovations of this portable device include: Efficient pre-screening of military personnel. Immediate post-accident screening of soldiers for TBI, including mTBI, in forward deployed areas of operation. Follow-up screening for assessing prescribed TBI or mTBI treatment. Use as a portable rehabilitation tool for mTBI patients. The device 10 provides Combined VR and visual stimulus with eye tracking technology in portable package. Remote data access from forward deployed facilities to other medical personnel for triage can be implemented.

Current development in 3-D and VR has produced continuous breakthroughs in the areas of science, medicine and military applications. At the heart of VR is the accelerated 3-D graphics hardware that has been doubling in performance every six months. The cost of PC hardware has also continued to decline. In the area of VR software, the landscape has greatly improved with new tools, web integration and a general acceptance of the new technology. New display technology aids VR in the areas of projection, screen technology and micro displays for head-mounted displays. New OLED micro displays are low power, easy to view, and compact. These improvements allow for a goggle based VR that can produce moving visual stimulus at simulated distances for a variety of neurologic tests of the present invention.

FIG. 1 is a schematic design of VOG/VNG unit 10 that includes the head-mounted goggles with the built-in 940 nm infrared micro LED 22 for illumination of the eyes 24 and the beam splitter plastic coated optic 14 that reflects visible light from OLED micro display 12. The setup allows reflected IR light from the eyes to be sent directly to the eye tracking miniature digital cameras 18 behind the mirrors 20. Simply, the VR screen 12 provides the visual stimulus and the cameras 18 capture eye 24 response for quick analysis and triage. The details of the VR display 12 are believed to be known to those or ordinary skill in the art and it allows the system 10 to present visual images or targets to the user that have a perceived or simulated distance much greater than the actual distance in the goggles. As a simple example the target could be a standard Eye Chart that is typically spaced 20 feet from the subject. The goggle VOG/VNG unit 10 of the present invention allow such a chart to be present to the subject on the goggle and would allow the operator to perform testing on such a chart without setting up an actual full scale system. The eye tracking technology is also known in the art, and the camera based eye tracking may use the IPORTAL® brand goggle based eye tracking cameras and software available from the assignee of this invention. FIG. 2 illustrates an alternative design having the display 12 in front of the user and the cameras 18 above. The assembly in FIG. 2 allows for two sets of optics 14, with the first primarily designed for proper field for the camera 18 while a second optic, behind the mirror 20, is designed to optimize for the display 12.

The combination of the eye tracking and the display of simulated distanced visual targets allow the VOG/VNG unit 10 to automatically run a number of preprogrammed neurologic tests and to record the physiologic responses thereto. Essentially the unit provides a full room sized visual testing platform in a single goggle mounting VOG/VNG unit 10.

The rational/purpose of the proposed system is to rapidly assess field-deployed personnel for potential TBI or mTBI. The technician in the field merely needs to put the unit on the subject and run the pre-identified tests. The contemplated system design will incorporate over 15 standard neurological tests simplified for a pass/refer criterion, that will facilitate rehabilitation and the monitoring of recovery and the compensation process. The device will provide a cost effective means to pre-screen soldiers prior to deployment to establish baseline brain function for future comparison if a future mTBI occurs. The device will allow full vestibular diagnostics and VOR rehabilitation for more in depth usage and follow up care.

This portable VR device will consist of: (a) rugged tablet PC, preferably meeting military specifications to provide for rugged use, equipped with software used to control the VR stimuli as well as to collect and analyze eye response data; (b) head mounted goggle with VR display used to present stimuli at the designated simulated distance for the test and integrated binocular eye tracking cameras.

The present invention provides a solution to overcome the limitations of existing screening, diagnostic and rehabilitation methods for mTBI patients. The proposed new system employs portable, head mounted VR eye tracking goggles from field to post-deployment. The system will incorporate efficient clinical diagnostic and screening methodologies for detecting mTBI related vestibular and neurological abnormalities. This technology will be instrumental in pre-screening, diagnosing and monitoring the progression of mTBI in soldiers who are deployed in remote locations, as well as those seeking post-deployment clinical services. Having the ability to collect objective, functional data will aid the clinicians in the diagnosis between mTBI and other psychological disorders.

The present invention uses analytical and 3-D design methods, in the development of anatomically and functionally correct head-mounted goggle that can accommodate existing VR optics and miniature digital cameras. The VR stimulus software is integrated into existing vestibular/neurological software for protocol setup, test results analysis, and to create VR stimulus.

The screening protocols of the googles 10 is anticipated to include the following standard tests horizontal and vertical calibration of subject eyes, nystagmus tests (horizontal, vertical and spontaneous), horizontal and vertical smooth pursuit, horizontal and vertical saccades, optokinetic tests, subjective visual horizontal and vertical and two rehabilitation protocols (exercises), one VOR and second optokinetic.

The invention may include the step of obtaining pre-trauma objective physiologic responses of the subject from the head mounted goggle unit based upon each of the visual stimulus presented to the subject, wherein the pre-trauma objective physiologic responses form a baseline for the subject. With a baseline the step of using the objective physiologic responses to diagnose the presence of traumatic brain injury includes a determining whether at least one post-trauma objective physiologic responses of the subject differs from the associated pre-trauma objective physiologic response by greater than a preset threshold for that response. Alternatively the invention may utilize a normative database of similar subjects (e.g. all med in their 20s, etc) whereby the step of using the objective physiologic responses to diagnose the presence of traumatic brain injury includes determining whether at least one post-trauma objective physiologic responses of the subject differs from an associated objective physiologic response of a normative database of similar subjects by greater than a preset threshold for that response. The baseline approach is preferred, but may not always be available VOG/VNG Unit 10 Protocol for Diagnosis of mTBI The following testing protocol represents one effective protocol under the invention for diagnosis of mTBI in patients. The protocol is performed with the VOG/VNG unit 10 and will be administered at each visit comprised of the following summary:

Pre-protocol calibration required each time prior to test administration (elapsed time—about 33 seconds) and followed by:

1. Horizontal random saccade (about 50 seconds)
2. Vertical random saccade (about 46 seconds)
3. Horizontal predictive saccade (about 20 seconds)
4. Smooth pursuit horizontal (3 frequencies) (about 33 seconds)
5. Smooth pursuit vertical (3 frequencies) (about 33 seconds)
6. Gaze Horizontal (alternatively Spontaneous nystagmus) (about 30 seconds)
7. Optokinetic (OKN) (2 tests) (about 31 seconds)
8. Antisaccade (about 1 minute 11 seconds)
9. Subjective visual vertical (about 24 seconds)
10. Subjective visual horizontal (about 37 seconds)
11. Visual reaction time (about 32 seconds)
12. Auditory reaction time (about 18 seconds)
13. Saccade and reaction time (about 1 minutes 2 seconds)
14. Light Reflex (about 45 seconds)

The total test battery time is less than 15 minutes per patient (approximately 13 minutes 30 seconds) and the unit 10 allows for the testing to progress in an almost fully automated method making it particularly easy for technicians. The technician merely needs to explain the upcoming or current test and review the results for testing abnormalities (e.g., results indicating the goggles have slipped off the patient, or the power has been interrupted, etc).

In the Horizontal random saccade (HS) the subject is directed to follow (or jump to) a target (the stimulus, such as a dot, although other stimulus may be utilized) as it is displayed at a fixed location on the screen. The visual stimulus is presented in this test at pseudo-randomly distributed times (between 1 to 2 seconds) and will exhibit displacements from −30 to +30 degrees measured along the horizontal axis. At least 30 trials or saccadic movements will be observed. The unit 10 will obtain values for at least eye peak velocity, latency, accuracy for both main saccade, and combined main and secondary corrective saccade. Corrective Saccadic movement and the measurement thereof is described in U.S. Patent Publication 2012-0081666 entitled "Method and Apparatus for Corrective Secondary Saccades Analysis with Video Oculography System", which is incorporated herein by reference Each variable is calculated separately for left and right eyes, and may be combined with movement in the left and right directions (Vertical saccade).

The main eye peak velocity during HS testing is a measure of the highest velocity during the main (or initial) saccadic eye movement and the corrective eye peak velocity is a measure of the highest velocity during the corrective saccadic movement. The unit 10 is configured to obtain a velocity measurement between every positional measurement of the eye. The peak eye velocity is believed to be a better biomarker than the average velocity, which is merely the total amount of eye movement from the beginning of the movement to the end of the main or corrective saccadic movement.

The main latency during the HS testing is the time duration from the initial display of the subject target or stimulus and the beginning of the main saccadic eye movement, while corrective latency is a measure of the time duration from the initial display of the subject target or stimulus and the beginning of the corrective saccadic eye movement. A more precise corrective latency is time duration from the initial display of the subject target or stimulus and the beginning of the corrective saccadic eye movement and minus the main latency and minus the duration of the main saccade movement.

The main accuracy is a ratio of the main saccadic movement over the target amplitude, such that values greater than 1 or 100% are "overshoots" and values under this are "undershoots" (although the ratio can easily be inverted).

The Vertical random saccade (VS) testing is analogous to HS testing in that the patient or subject is directed to follow (or jump to) a target stimulus on the display 12 (such as a dot) as it is displayed at pseudo-randomly distributed times (between 1 to 2 seconds) and displacements (from −20 to +20 degrees) along the vertical axis. Thirty (30) trials or targets for VS testing are presented. As with HS testing, in VS testing the unit 10 will obtain values for at least eye peak velocity, latency, accuracy for both main saccade, and combined main and secondary corrective saccade. Each variable is calculated separately for left and right eyes, and may be combined with movement in the up and down directions (the HS testing).

In the Horizontal predictive saccade (HPS) testing the subject is directed to view a visual stimulus as it is quickly displayed at a fixed location. Subject will be presented with 6 pseudo-random saccade stimuli followed by 20 "mirrored" saccade stimuli meaning these have a repeated displacement of +/−10 degrees in the horizontal direction and the stimuli are presented at a constant time interval of 0.65 seconds.

In the HPS testing the unit 10 will measure the first predicted saccade which is the number of mirrored saccade stimuli until the main latency is less than zero for that stimuli trial, although a number slightly higher than zero could be used as such could still be indicative of a predictive aspect if the number was small enough. Most subjects will reach a predictive saccade within several repetitions. In the HPS testing the unit 10 will measure the percentage of predicted saccades which is merely the number of saccadic stimuli having the latency lower than zero (or a slightly higher threshold than zero, if desired) divided by the total number of mirrored stimulus. As noted from this description, in the HPS testing the unit 10 will measure the main saccade latency. Each variable may be calculated separately for left and right eyes in HPS testing.

In the Smooth pursuit horizontal (SPH) testing the subject is directed to follow a visual stimulus (e.g. a dot on screen 12) as it moves through a sinusoidal displacement of +/−10 degrees along the horizontal axis. The SPH testing is run at three distinct frequencies, namely at frequencies of: (1) 3 cycles at 0.1 Hz; (2) 5 cycles at 0.75 Hz; and (3) 7 cycles at 1.25 Hz.

In SPH testing the unit 10 measures the Velocity gain (also called the pursuit gain) to the right and to the left. The velocity gain is ratio of the eye velocity to the target velocity. In SPH testing the unit 10 measures the velocity gain asymmetry which is the difference between the gain to the right and to the left. In SPH testing the unit 10 measures velocity phase to the right and to the left which is a measure of the patient eye velocity relative to the target velocity profile. In SPH testing the unit 10 measures the percent of saccade, which is the percent of saccadic eye movement components that comprise the whole of the smooth pursuit test. In SPH testing the unit 10 measures the position gain to the right and to the left which is comparison of the eye position to the target position and asymmetry values between right and left. In SPH testing the unit 10 provides a spectral purity measurement and an initiation latency measurement. The SPH testing may provide values separately for the left and right eyes.

In Smooth pursuit vertical (SPV) testing the subject is directed to follow a target as it moves through a sinusoidal displacement of +/−10 degrees along the vertical axis, analogous to the SPH testing discussed above. The SPV testing is run at frequencies of: (1) 3 cycles at 0.1 Hz; (2) 5 cycles at 0.75 Hz; and (3) 7 cycles at 1.0 Hz. The SPV variables are the same as SPH testing discussed above.

In Gaze Horizontal (GH) testing the subject is directed to fixate on a target light or stimulus for 3 seconds, which target is located 10° to the right of a origin or center position. The stimulus or Light is then extinguished for 15 seconds. The subject is directed to fixate on a target light for 3 seconds, which is located 10° to the left of center. Light is then extinguished for 15 seconds. The unit 10 will calculate Peak slow phase velocity for horizontal and vertical eye movement components with and without the target or fixation light on. The SPH testing may provide values separately for the left and right eyes.

In the two Optokinetic (OKN) tests the patients will see stimulus (e.g., lighted dots moving on the display first to the right, then to the left. The two optokinetic stimulus will be at rotation rates or speeds of 20 and 60 deg/sec, respectively. Each test consists of 15 seconds clockwise (CW) and 15 seconds counterclockwise (CCW) rotation stimulus. The unit 10 will measure at least the Average slow phase gain, average slow phase asymmetry, fast phase velocity vs. amplitude, and fast phase velocity asymmetry for each test and for left and right eyes.

In the Antisaccade (AS) testing the subjects or patients are required to fixate on a central target for 1.5 to 2.5 seconds and then presented with a peripheral target; patients are instructed to generate an eye movement in the same distance as the target displacement, but in the exact opposite direction. Patients are trained using slow presentations of the task during which a technician provides verbal instructions about task demands and appropriate responses (training test). The measured testing constitutes 20 anti-saccades stimulus with time between saccades randomly selected from 1 to 2 seconds and random displacement for each target of between −30 to +30 degrees. The unit 10 measures Pro-saccade error (also called an anti-suppression error) measurement, anti-saccade latency (measure from the stimulus to the start of the anti-saccadic eye movement), latency of pro-saccade error (generally the main saccadic latency), anti-saccade peak velocity, accuracy of main anti-saccade, and accuracy of main and corrective anti-saccades. The AS testing measurements may be for each of the left and right eyes.

In the subjective visual vertical (SVV) testing the subject is presented with a red line on the display and directed to use control left and right buttons (or any desired input device such as a joystick etc) to manipulate the displayed line into the vertical (upright). One input button rotates the line in one direction and the other input device rotates the line in the other. Subject is directed to inform the clinician when they are finished and they believe the line is vertical, known as the the subjective vertical position. The unit 10 measures the mean and standard deviation from subjective vertical position and the true vertical position.

In the subjective visual Horizontal (SVH) testing the subject is presented with a red line on the display and directed to use control left and right buttons (or any desired input device such as a joystick etc) to manipulate the displayed line into the horizontal (flat). One input button rotates the line in one direction and the other input device rotates the line in the other. Subject again is directed to inform the clinician when they are finished and they now believe the line is horizontal, known as the subjective horizontal position. The unit 10 measures the mean and standard deviation from subjective horizontal position and the true horizontal position.

In the Visual reaction time (VRT) test 20 random time center lights or stimulus are presented. The subject is directed to signal their recognition by pressing a button, or other input. The system 10 measures the Average visual reaction time and the standard deviation (SD) of the reaction time.

In the Auditory reaction time (ART) test 20 random pulses of sound are presented to the subject through an associated audio output (speaker) and the subject is directed to signal their recognition by pressing a button. The 10 measures the Average audio reaction time and the SD of the reaction time.

In the Saccade and reaction time (SVRT) test 30 visual saccadic stimuli are randomly projected from 1 to 2 seconds and displacement of −30 to +30 degrees. The patients is directed to gaze at the saccadic stimulus and then also press either the left or right button (or other input device) to record whether the stimulus was projected to the right or to the left. The unit 10 measures the same descriptive variables as regular saccade (HS and VS) along with latency, SD, and percent of error for each direction.

In Light Reflex (LR) testing a central stimulus (e.g. a light spot or dot) is projected for 300 milliseconds and extinguished for 3 seconds and the sequence will be repeated 10 times. The system measures pupil reaction latency, constriction velocity, and amplitude separately for the left and right eyes.

The comprehensive I-Portal® system based neuro-otologic test device 10 described above is an effective diagnostic tool for mTBI detection and to monitor recovery from head trauma. The I-Portal® system based neuro-otologic tests are neuro-physiologic; measuring the eye's response to various motion, oculomotor, and optokinetic stimuli. Initial data shows I-Portal® tests described above can detect abnormalities resulting from head trauma even when structural imaging technologies show no damage. The test battery also suggests the data is significantly more objective than current neuro-psychological tests that rely partially on patient self diagnosis. See the testing results in a 2010 study entitled "Early Results of Optical and Vestibular Reflex Testing in Concussions" by Sam Akhaven, MD, Alex Kiderman PHD, Erik Happ, MD, Edward Snell, MD & Patrick J. Demeo, MD, presented by the Allegheny General Hospital Sports Medicine Department and available at the West Penn Allegheny Health System website: www.wpahs.org.

The unit 10 is and may continue to be used by military and sports medicine researchers to study new methods to objectively diagnose and monitor blast and blunt force head trauma. The above described battery of tests help examiners make better return to play and return to duty decisions. The abnormal results, based upon an individual baseline or a normative group, to the above battery of tests presents a effective screening tool for an increased likelihood of the presence of mTBI.

Example of Noninvasive Rapid Screening of Mild Traumatic Brain Injury Using Combination of Subject's Objective Oculomotor, Vestibular and Reaction Time Analytic Variables as Shown in the Attached Poster/Figure The following describes a method for detecting the presence, and assessing the severity of a concussion (or a mild traumatic brain injury, or mTBI) in any patient presenting to a clinical professional, who is suspected of having a concussion/mTBI following a precipitating head injury. Specifically, the following describes the process by which the method is developed and applied.

A battery of vestibular, oculomotor, and reaction time tests are administered to a cohort of mTBI patients and an age-matched control population. This battery associated with this example is listed below. The battery is performed on devices capable of providing visual and auditory stimuli to a subject, measuring eye movements at a rate of at least 100 Hz, and capturing button presses at a comparable rate.

Analytic variables derived from these tests (447 variables) are listed below in this example. After collection of these variables, a critical subset is identified by a three step process:

1. The variable set is reduced by factor analysis. This reduces the original variable set to a first subset of variable, in this particular example from 447 to 82 variables.
2. A preliminary logistic regression is performed on the initial subset 82 variables, coding mTBI patients as 1 and controls as 0. As a product of this process, a Wald statistic is generated for each variable. All variables with a p (probability) value >a preset threshold, such as 0.05, for the Wald statistic are removed. This reduces the variable set to a second subset of variables, specifically 33 variables in this example.
3. Step 2 is repeated: A second linear regression is performed on the second subset of variables and variables with Wald statistic p-values >a preset threshold, again such as 0.05, are again removed. This reduces the variable set to a final desired set, namely 8 variables in the specific example.

To create an assessment model, a third logistic regression is performed on these 8 variables, which generates a set of 8 coefficients. A cutoff value (in the range of 0 to 1) is chosen as a threshold value. Assessment is performed by administering the same test battery and recording (at the minimum) the eight measures determined to be critical variables. These variables are used as input parameters to the assessment model, and a result between 0 and 1 is produced. Presence of mTBI is determined categorically by relationship to the chosen cutoff, i.e. patients with scores above the cutoff are categorized as having a concussion mTBI, or screening positive for the presence of a concussion/mTBI. Severity of mTBI is determined parametrically by the magnitude of the assessment model output, with 1 representing the most severe cases.

The final set of 8 variables for this particular example is as follows:

Optokinetic nystagmus, gain of eye relative to stimulus
Subjective visual line placement, mean error in degrees
Horizontal smooth pursuit, presence of saccades
Horizontal smooth pursuit, phase lag of eye
Auditory reaction time variability
Latency to onset of vertical smooth pursuit tracking
Combined saccade+ reaction time, latency of saccades
Vertical smooth pursuit, upward phase lag of eye It should be understood that the exact number of initial variables (here, 447 listed below) will depend on the exact construction of the test battery. The battery described below yields the variables listed below, and these variables are by no means an exhaustive list of measures that can be acquired with devices like those described. All other numbers described in this example will depend on the exact population of patients and control subjects used to generate the assessment model. Since the Wald statistic is dependent on the standard error of a measure and the coefficient that regression assigns (which is, in turn, dependent upon the relative distribution of the values of all measures across all subjects), it is unlikely that the numbers described in this example will be the same for any two populations (for any two applications of this method of developing an assessment model). Numbers affected by these issues are: the first subset of 82 variables resulting from reduction by factor analysis, the second subset of 33 variables resulting from Wald statistic reduction, and the 8 variables resulting from the second Wald statistic reduction.

For the same reasons, the exact variable sets that are generated at each reduction step (which variables are retained) will also vary based on the initial population. The number and membership of each variable set at each reduction step will also change if any of a multitude of (equally valid) statistical procedures are applied in lieu of factor analysis or logistic regression (e.g. discriminate analysis, non-parametric classifiers such as decision tree, support vector machine, neural network analysis, etc.).

Test Battery

| TEST | mTBI Study Protocol | Example measures |
|---|---|---|
| Spontaneous nystagmus | 1 cycle - Stimulus light is projected at a central fixation point for 3 seconds, followed by light off for 15 seconds. | Amount, rate, and direction of spontaneous nystagmus |
| Optokinetic nystagmus | 2 cycles - Full field random dot stimulus continually moves left 10 seconds, and then right 10 seconds, at 20°/second and 60°/second velocity | Integrity of fixation reflex combining pursuits and saccades |
| Smooth pursuit - horizontal | Single light stimulus moves smoothly left, then right, with sinusoidal velocity and maximum displacement of 10°. 3 cycles at 0.1 Hz, 5 cycles at 1.0 Hz, 7 cycles at 1.25 Hz. | Gain of eye relative to stimulus; presence of saccadic intrusions |
| Smooth pursuit - vertical | Same as horizontal, but with 5 cycles at 0.75 Hz, 7 cycles at 1.0 Hz. | Same |
| Saccade - random horizontal | 30 cycles - Single light stimulus projected at random horizontal displacements and time, with maximum displacement of 30°, and time between stimuli 1.2 to 2.0 seconds. | Saccade onset latency, accuracy, presence of corrective saccades |
| Saccade - random vertical | Same as horizontal, but with maximal vertical displacement of 20°. | Same |
| Saccade - predictive horizontal | 20 cycles - Single light stimulus is projected at 10° left or right displacement (alternating) with a fixed 0.65 second interval. | Ability to adapt to predictable timing and position (latency and accuracy of saccades) |
| Saccade - predictive vertical | Same as horizontal, using 10° up and down displacements. | Same |
| Saccade - antisaccade horizontal | Same as Saccade - random horizontal, except that subject is instructed to look away from the target. | Number of incorrect pro-saccades, corrective anti-saccades; latency |

-continued

| TEST | mTBI Study Protocol | Example measures |
|---|---|---|
| Saccade and reaction time | Single light stimulus projected at random horizontal displacements and time, with maximum displacement of 30°, and time between stimuli 1.2 to 2.0 sec, subject asked to click left or right buttons depends on direction of saccades. | Saccade onset latency, accuracy, presence of corrective saccades, latency and S.D. for left and right buttons |
| Visual Reaction time | 20 cycles, random single light stimulus appears at center of vision and subject using his/her dominate hand click on button on | Latency and latency standard deviation |
| Auditory reaction time | 20 cycles, random auditory stimulus 85 decibel presented and subject using his/her dominate hand click on button as stimulus on | Latency and latency standard deviation |
| Subjective visual - vertical | 6 cycles - Straight line stimulus appears tilted off vertical axis, up to 30° displacement clockwise or counterclockwise. Subject asked to press buttons to tilt line back to vertical alignment. | Angular error from vertical axis |
| Subjective visual - horizontal | 6 cycles - Same as vertical, except asked to tilt line until it is horizontal. | Angular error from horizontal axis |

The above protocol results in effective parameters for summarizing the system of the present invention. Broadly the present invention provides the use of 5-15, preferably 8-10, of the list of 440+ occulomotor, vestibular and reaction time measures to screen for the presence of mTBI. More narrowly the present invention provides the use of 5-15, preferably 8-10, of the list of 82 variables obtained after conducting a conventional dimension reduction by factor analysis on the 440+ occulomotor, vestibular and reaction time measures to screen for the presence of mTBI. Alternatively the invention may be described as the use of 5-15, preferably 8-10, of a subset of variables selected using conventional Wald Statistical Analysis with p>0.03 to p>0.09, generally p>0.05, on the list of 82 variable obtained after conducting a conventional dimension reduction by factor analysis on the 440+ occulomotor, vestibular and reaction time measures to screen for the presence of mTBI. Alternatively the invention may be described as the use of 5-15, preferably 8-10, variable that are identified using conventional Wald Statistical Analysis with p>0.03 to p>0.09, generally p>0.05, of a subset of variables selected using conventional Wald Statistical Analysis with p>0.03 to p>0.09, generally p>0.05, on the list of 82 variable obtained after conducting a conventional dimension reduction by factor analysis on the 440+ occulomotor, vestibular and reaction time measures to screen for the presence of mTBI.

It is understood, therefore, that this invention is not limited to the particular embodiments disclosed, but it is intended to cover modifications that are within the spirit and scope of the invention, as defined by the appended claims and equivalents thereto. The preferred embodiments described above are illustrative of the present invention and not restrictive hereof. It will be obvious that various changes may be made to the present invention without departing from the spirit and scope of the present invention. The precise scope of the present invention is defined by the appended claims and equivalents thereto.

What is claimed is:

1. A method of diagnosis of mild traumatic brain injury or concussion comprising the steps of:
   providing a head mounted goggle based stimulus generating eye tracking unit to the subject;
   presenting visual stimulus to the subject, wherein the visual stimulus is in the head mounted goggle based system and forms the optical target stimulus for at least a nystagmus test;
   obtaining objective physiologic response of the subject from the eye tracking within the head mounted goggle unit based upon each of the visual stimulus presented to the subject in each test; and
   using the objective physiologic responses to diagnose the presence of mild traumatic brain injury or concussion.

2. The method of diagnosis of mild traumatic brain injury or concussion according to claim 1, further including the step of obtaining pre-trauma objective physiologic responses of the subject from the head mounted goggle unit based upon each of the visual stimulus presented to the subject, wherein the pre-trauma objective physiologic responses form a baseline for the subject.

3. The method of diagnosis of mild traumatic brain injury or concussion according to claim 2, wherein the step of using the objective physiologic responses to diagnose the presence of mild traumatic brain injury or concussion includes a determining whether at least one post-trauma objective physiologic responses of the subject differs from the associated pre-trauma objective physiologic response by greater than a preset threshold for that response.

4. The method of diagnosis of mild traumatic brain injury or concussion according to claim 1, wherein the visual stimulus presented to the subject includes at least one spontaneous nystagmus test.

5. The method of diagnosis of mild traumatic brain injury or concussion according to claim 1, wherein the visual stimulus presented to the subject further includes at least one horizontal nystagmus test, one vertical and one spontaneous nystagmus test.

6. The method of diagnosis of mild traumatic brain injury or concussion according to claim 1, wherein the visual stimulus presented to the subject further includes at least one horizontal smooth pursuit test and at least one vertical smooth pursuit test.

7. The method of diagnosis of mild traumatic brain injury or concussion according to claim 1, wherein the visual stimulus presented to the subject further includes at least one horizontal saccades test and at least one vertical saccades test.

8. The method of diagnosis of mild traumatic brain injury or concussion according to claim 1, wherein the step of using the objective physiologic responses to diagnose the presence of traumatic brain injury includes a determining whether at least one post-trauma objective physiologic responses of the subject differs from an associated objective physiologic response of a normative database of similar subjects by greater than a preset threshold for that response.

9. A method of diagnosis of traumatic brain injury comprising the steps of:
   providing a tracking goggle unit coupled to the subject having onboard digital cameras directed to the subjects eyes and onboard display generating stimulus for the subject;
   presenting a plurality of visual stimulus to the subject on the goggle mounted display, wherein each visual stimulus Is presented in the eye tracking unit, wherein each visual stimulus provides a target stimulus for a distinct visual based neurologic test;

obtaining objective physiologic response of the subject from the eye tracking unit based upon each of neurologic test associated with each visual stimulus presented to the subject; and using the objective physiologic responses to the neurologic tests to diagnose the presence of traumatic brain injury.

10. The method of diagnosis of traumatic brain injury according to claim 9, wherein the visual stimulus presented to the subject includes at least one nystagmus test.

11. The method of diagnosis of traumatic brain injury according to claim 9, wherein the visual stimulus presented to the subject includes at least one horizontal nystagmus test, one vertical and one spontaneous nystagmus test.

12. The method of diagnosis of traumatic brain injury according to claim 9, wherein the visual stimulus presented to the subject includes at least one horizontal smooth pursuit test and at least one vertical smooth pursuit test.

13. The method of diagnosis of traumatic brain injury according to claim 9, wherein the visual stimulus presented to the subject includes at least one horizontal saccades test and at least one vertical saccades test.

14. The method of diagnosis of traumatic brain injury according to claim 9, wherein the step of using the objective physiologic responses to diagnose the presence of traumatic brain injury includes a determining whether at least one post-trauma objective physiologic responses of the subject differs from an associated objective physiologic response of a normative database of similar subjects by greater than a preset threshold for that response.

15. The method of diagnosis of traumatic brain injury according to claim 9, further including the step of obtaining pre-trauma objective physiologic responses of the subject from the head mounted goggle unit based upon each of the visual stimulus presented to the subject, wherein the pre-trauma objective physiologic responses form a baseline for the subject.

16. The method of diagnosis of traumatic brain injury according to claim 15, wherein the step of using the objective physiologic responses to diagnose the presence of traumatic brain injury includes a determining whether at least one post-trauma objective physiologic responses of the subject differs from the associated pre-trauma objective physiologic response by greater than a preset threshold for that response.

17. The method of diagnosis of traumatic brain injury according to claim 16, wherein the visual stimulus presented to the subject includes at least one nystagmus test.

18. The method of diagnosis of traumatic brain injury according to claim 16, wherein the visual stimulus presented to the subject includes at least one horizontal nystagmus test, one vertical and one spontaneous nystagmus test.

19. The method of diagnosis of traumatic brain injury according to claim 17, wherein the visual stimulus presented to the subject includes at least one horizontal smooth pursuit test and at least one vertical smooth pursuit test.

20. A method of screening for mild traumatic brain injury or concussion comprising the steps of:

providing a head mounted goggle based stimulus generating eye tracking unit to the subject;

Performing a battery of tests on the subject through the head mounted goggle based stimulus generating eye tracking unit, the testing battery including at least one random saccade test; at least one predictive saccade test; at least one smooth pursuit test; at least one gaze test, at least one anti-saccade test; at least one of a subjective vertical or a subjective horizontal test; and at least one reaction time test; and Indicating an increased likelihood of mild traumatic brain injury or concussion based upon abnormal results to this battery of tests.

* * * * *